United States Patent
Kendrick et al.

(10) Patent No.: US 12,121,666 B2
(45) Date of Patent: *Oct. 22, 2024

(54) FLUID TRAP APPARATUS

(71) Applicant: SunMed Group Holdings, LLC, Grand Rapids, MI (US)

(72) Inventors: Paul Kendrick, Baltimore, MD (US); Mark Woelfel, Oak Ridge, NJ (US)

(73) Assignee: SunMed Group Holdings, LLC, Grand Rapids, MI (US)

( * ) Notice: Subject to any disclaimer, the term of this patent is extended or adjusted under 35 U.S.C. 154(b) by 794 days.

This patent is subject to a terminal disclaimer.

(21) Appl. No.: 17/213,988

(22) Filed: Mar. 26, 2021

(65) Prior Publication Data

US 2021/0213232 A1 Jul. 15, 2021

Related U.S. Application Data

(63) Continuation of application No. 15/925,387, filed on Mar. 19, 2018, now Pat. No. 11,007,338, which is a continuation of application No. 13/692,245, filed on Dec. 3, 2012, now Pat. No. 9,919,122.

(51) Int. Cl.
*A61M 16/08* (2006.01)

(52) U.S. Cl.
CPC ..... *A61M 16/0808* (2013.01); *A61M 16/0833* (2014.02); *A61M 16/0875* (2013.01)

(58) Field of Classification Search
CPC ............ A61M 16/0808; A61M 16/085; A61M 16/0875; A61M 16/1045; A61M 16/0833
See application file for complete search history.

(56) References Cited

U.S. PATENT DOCUMENTS

| | | | |
|---|---|---|---|
| 4,327,718 A | 5/1982 | Cronenberg | |
| 4,457,305 A | 7/1984 | Shanks et al. | |
| 4,867,153 A | 9/1989 | Lorenzen et al. | |
| 5,121,746 A | 6/1992 | Sikora | |
| 5,168,868 A | 12/1992 | Hicks | |
| 5,228,436 A | 7/1993 | Parkin | |
| 5,398,677 A | 3/1995 | Smith | |
| 5,830,185 A * | 11/1998 | Block, Jr. | A61M 16/085 604/122 |
| D405,522 S | 2/1999 | Hoenig et al. | |
| 6,394,142 B1 | 5/2002 | Woelfel et al. | |
| 8,156,935 B2 | 4/2012 | Chang | |
| 8,215,304 B2 | 7/2012 | Reinboth et al. | |
| 8,236,081 B2 | 8/2012 | Roth et al. | |
| 9,095,675 B2 | 8/2015 | Stjernfelt et al. | |
| 2002/0148464 A1 | 10/2002 | Hoenig | |
| 2005/0188990 A1 | 9/2005 | Fukunaga et al. | |
| 2010/0122702 A1 | 5/2010 | Reinboth et al. | |
| 2010/0252035 A1 | 10/2010 | Chang | |
| 2012/0266888 A1 | 10/2012 | Dwyer et al. | |

* cited by examiner

*Primary Examiner* — Margaret M Luarca
(74) *Attorney, Agent, or Firm* — Sheridan Ross P.C.

(57) ABSTRACT

A fluid trap is disclosed herein. The fluid trap has a reservoir housing defining a reservoir and a tube connector coaxially disposed through the reservoir housing. The tube connector has first and second connector ends extending from opposing sides of the reservoir, an interior passageway in fluid communication with the first and second connector ends, and an aperture in fluid communication with the reservoir. The reservoir is in fluid communication with the interior passageway and is configured to retain fluid from that passageway.

19 Claims, 4 Drawing Sheets

FLUID TRAP APPARATUS

CROSS-REFERENCE TO RELATED APPLICATIONS

This application is a continuation of U.S. patent application Ser. No. 15/925,387 entitled "FLUID TRAP APPARATUS," and filed on Mar. 19, 2018, which is a continuation of U.S. patent application Ser. No. 13/692,245 entitled "FLUID TRAP APPARATUS," and filed on Dec. 3, 2012, which issued on Mar. 20, 2018, as U.S. Pat. No. 9,919,122, the disclosures of which are hereby incorporated by reference in their entirety.

BACKGROUND

Anesthetic and respirator breathing devices commonly include a breathing circuit to direct gas flow to and away from the patient. The breathing circuit may include breathing circuit tubes, connectors and a patient interface. One category of breathing circuit tubes comprises dual lumen tubes. Dual lumen tubing refers generally to a single tubular apparatus with a partition separating the tube interior into two distinct lumens or channels. The two lumens may be implemented to separately accommodate a patient's inspiratory flow and expiratory flow within a single apparatus.

One problem with conventional dual lumen breathing circuit tubing is that condensation in the expiratory gas may accumulate in one of the lumen, and accumulated fluid can cause an occlusion.

SUMMARY

The above-mentioned shortcomings, disadvantages and problems are addressed herein which will be understood by reading and understanding the following specification.

One or more embodiments include a fluid trap, according to aspects of the disclosure. The fluid trap includes a reservoir housing defining a reservoir and a tube connector disposed through the reservoir housing. The tube connector includes a first connector end extending outward from a first side of the reservoir housing, a second connector end extending outward from a second side of the reservoir housing, an interior passageway in fluid communication with the first connector end and the second connector end, and an aperture defined by the interior passageway, the aperture in fluid communication with the reservoir, wherein the reservoir housing and the tube connector are coaxial.

One or more embodiments include a fluid trap, according to aspects of the disclosure. The fluid trap includes a cylindrical reservoir housing defining a plurality of reservoirs fluidly separated by an interior partition and a tube connector disposed coaxially through the reservoir housing. The tube connector includes a first connector end extending outward from a first side of the reservoir housing, a second connector end extending outward from a second side of the reservoir housing, a plurality of interior passageways in fluid communication with the first connector end and the second connector end, the plurality of interior passageways fluidly separated from one another, and a plurality of apertures, each aperture defined by one of the plurality of interior passageways and in fluid communication with one of the plurality of reservoirs.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
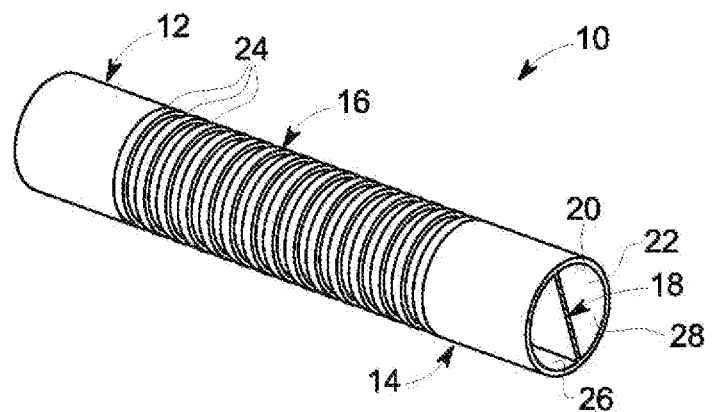
FIG. 1 is a perspective view of a dual lumen tube in accordance with an embodiment.

Referring to FIG. 1, a perspective view of a tube 10 is shown tube in accordance with an embodiment. The tube 10 will be described as a breathing circuit tube for use with healthcare devices such respiratory or anesthesia machines, however alternate applications may be envisioned. According to one embodiment the tube 10 may be implemented to deliver inspiratory gas from an anesthesia machine to a patient (not shown), and to transfer expiratory gas from the patient to a scavenging system (not shown). Scavenging systems may be implemented to recycle exhaled anesthetic agent and are well known by those skilled in the art.

The tube 10 comprises a first terminal end portion 12, a second terminal end portion 14, a body 16 defined between the end portions 12, 14, and a partition or septum 18. The tube 10 is generally hollow defining an interior surface 20 and a channel 22. The terminal end portions 12, 14 are cylindrical with a smooth exterior surface adapted to facilitate an airtight coupling when connected to another device.

According to one embodiment, the body 16 may define a plurality of corrugations 24. The corrugations 24 provide flexibility thereby allowing for optimal placement and routing of the tube 10 in a potentially restricted environment. The partition 18 may be secured to the interior surface 20 of the tube 10. The partition 18 may define a flat geometry extending from a first portion of the interior surface 20 to a second generally opposite portion of the interior surface 20. In the manner described, the partition 18 bisects the channel 22 defining a dual lumen configuration comprising a first lumen 26 and a second lumen 28.

The dual lumen configuration can facilitate the transfer of inspiratory gasses to a patient and expiratory gasses from a patient with a single apparatus. For illustrative purposes, the tube 10 will hereinafter be described as being connected such that inspiratory gas is transferred from an anesthesia machine to a patient (not shown) via the first lumen 26, and expiratory gas is transferred from the patient to a scavenging system (not shown) via the second lumen 28.

Fluid from condensation can accumulate within the tube 10. As condensation is generally present only in expiratory gas, fluid only accumulates in lumen 28. It is preferable to transfer this fluid into a retainer or trap to avoid an occlusion.

Figure 2:
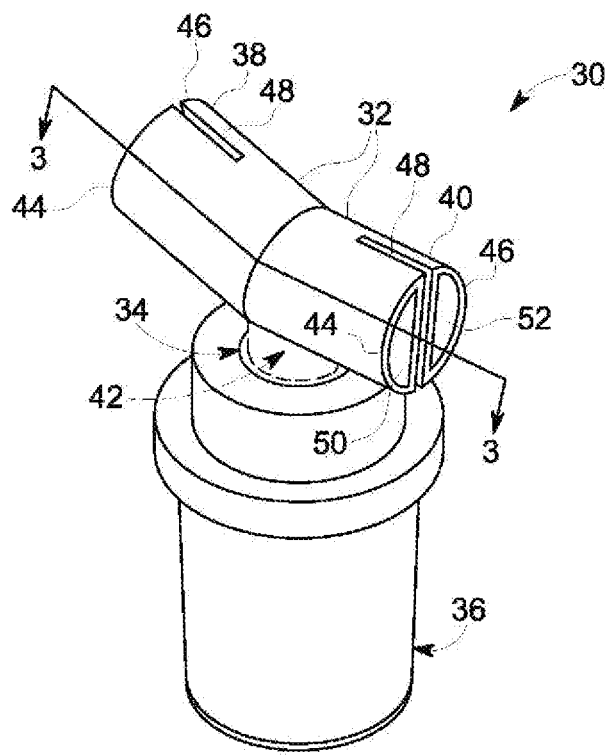
FIG. 2 is a perspective view of a fluid trap in accordance with an embodiment.

Referring now to FIG. 2, a fluid trap 30 is shown in accordance with an embodiment. The fluid trap 30 comprises a tube connector 32, a reservoir interface 34 and a reservoir 36. The tube connector 32 comprises a first end 38 and a second end 40. The connector ends 38, 40 will hereinafter be described in accordance with the depicted embodiment as being adapted for insertion into separate dual lumen tubes, however alternate connections can be envisioned. When inserted in this manner, the coupled components functionally form a single dual lumen apparatus with an integral fluid trap.

The reservoir interface 34 is hollow defining an interior conduit 42 in fluid communication with the reservoir 36. The reservoir 36 is designed to retain fluid from the tube 10. When the reservoir 36 becomes full of fluid it can be drained or replaced with minimal breathing circuit interference.

The connector ends 38, 40 define a generally cylindrical exterior formed by two back-to-back, outward facing D-shaped portions 44, 46 with a gap 48 therebetween. The D-shaped portions 44, 46 are hollow and respectively define interior passages 50, 52 extending through the entire length of the tube connector 32. The interior passages 50, 52 are discrete in order to maintain separation between transferred gases. The gap 48 is adapted to accommodate the tube partition 18 (shown in FIG. 1). The two D-shaped portions 44, 46 are adapted for insertion into a dual lumen tube such that one of the D-shaped portions is inserted into a first lumen, and the other of the D-shaped portions is inserted into the second lumen.

Figure 3:
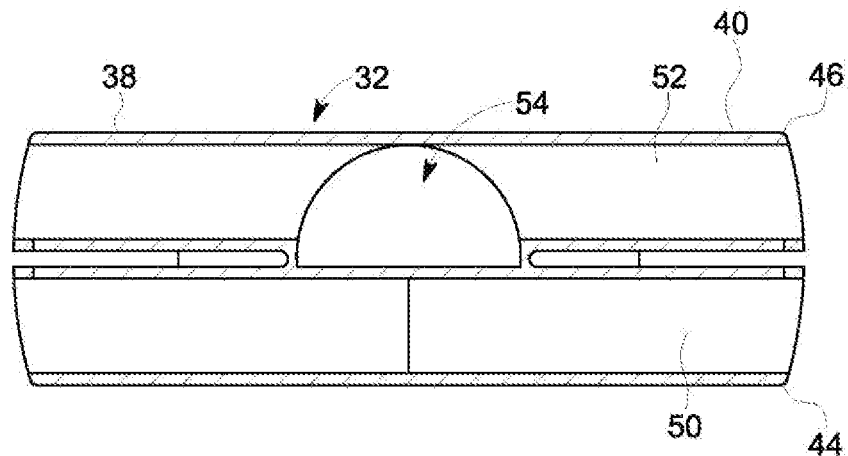
FIG. 3 is a cross-sectional view of a tube connector from FIG. 2 accordance with an embodiment.

Referring to FIG. 3, a sectional view of the tube connector 32 through section 3-3 of FIG. 2 is shown in accordance with an embodiment. The interior passage 52 is in fluid communication with an aperture 54 located approximately half-way between connector end 38 and connector end 40. The aperture 54 is in fluid communication with the reservoir interface conduit 42 (shown in FIG. 2). When the D-shaped portion 46 is inserted into or otherwise coupled with the lumen 28, the reservoir 36 (shown in FIG. 2) is preferably oriented downward. Gravity directs fluid from expiratory gas in the lumen 28 through the aperture 54, through the reservoir interface conduit 42, and into the reservoir 36.

As the interior passage 50 is adapted to accommodate inspiratory gas, and inspiratory gas does not comprise fluid, there is no need to couple the interior passage 50 with the reservoir 36 (shown in FIG. 2). Accordingly, the interior passage 50 merely forms a pass through connection. The fluid trap 30 is unidirectional meaning that D-shaped portion 46 must be coupled with the expiratory lumen 28, and D-shaped portion 44 must be coupled with the inspiratory lumen 26.

Figure 4:
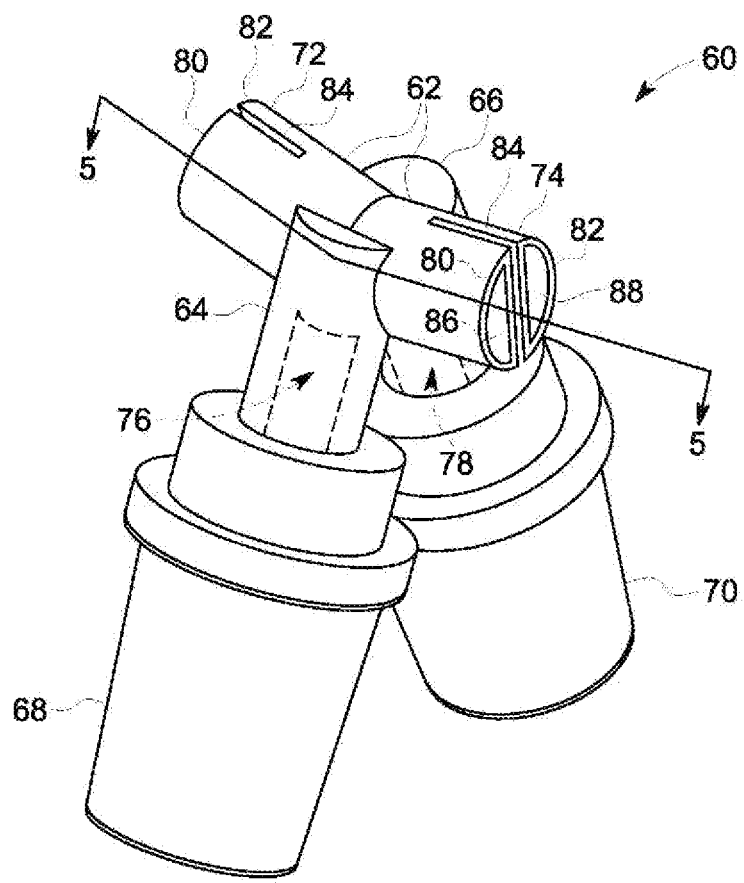
FIG. 4 is a perspective view of a fluid trap in accordance with an embodiment of the present invention.

Referring to FIG. 4, a dual reservoir fluid trap 60 is shown in accordance with another embodiment. The fluid trap 60 comprises a tube connector 62, a first and second reservoir interface 64, 66, and a first and second reservoir 68, 70. The tube connector 62 comprises a first end 72 and a second end 74. The connector ends 72, 74 will hereinafter be described in accordance with the depicted embodiment as being adapted for insertion into separate dual lumen tubes, however alternate connections can be envisioned.

The reservoir interfaces 64, 66 are both hollow, respectively defining interior conduits 76, 78. The interior conduit 76 is in fluid communication with the reservoir 68, and the interior conduit 78 is in fluid communication with the reservoir 70.

The connector ends 72, 74 define a generally cylindrical exterior formed by two back-to-back, outward facing D-shaped portions 80, 82 with a gap 84 therebetween. The D-shaped portions 80, 82 are hollow and respectively define interior passages 86, 88 extending through the entire length of the tube connector 62. The interior passages 86, 88 are discrete in order to maintain separation between transferred gases. The D-shaped portions 86, 88 and gap 84 are adapted for connection with a dual lumen tube in a manner similar to that previously described with respect to the fluid trap 30 (shown in FIG. 2).

Figure 5:
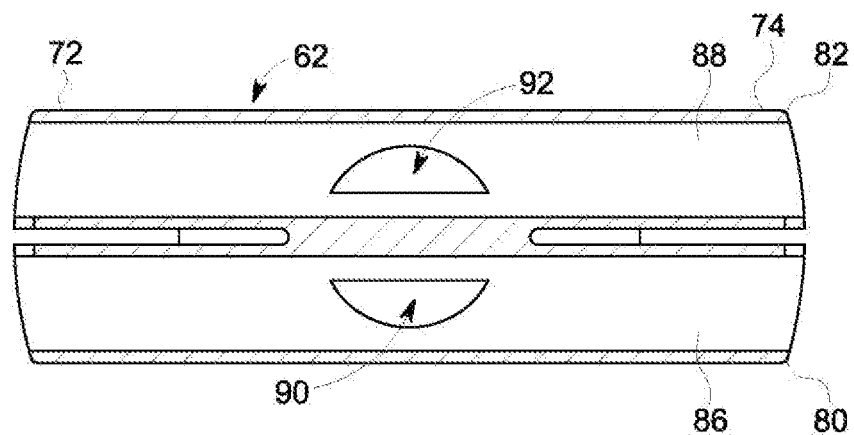
FIG. 5 is a cross-sectional view of a tube connector from FIG. 4 in accordance with an embodiment.

Referring to FIG. 5, a sectional view of the tube connector 62 through section 5-5 of FIG. 4 is shown in accordance with an embodiment. The interior passages 86, 88 are respectively in fluid communication with apertures 90, 92 located approximately half-way between connector end 72 and connector end 74. The apertures 90, 92 are each in fluid communication with one of the reservoir interface conduits 76, 78. When the D-shaped portions 80, 82 are inserted into or otherwise coupled with the lumen 26, 28, the reservoirs 68, 70 are preferably oriented downward. Gravity directs fluid in the lumen 26, 28 through one of the apertures 90, 92, through a respective reservoir interface conduit 76, 78, and into a respective reservoir 68, 70.

Because fluid only accumulates from expiratory gas, only one of the reservoirs 68, 70 is intended to collect fluid while the other remains empty. An advantage of the dual reservoir design of the fluid trap 60 (shown in FIG. 4) is that it is bidirectional meaning that D-shaped portions 80, 82 can each be coupled with either an inspiratory or expiratory lumen. The bidirectional design simplifies the process of connecting the fluid trap 60 and reduces the likelihood of user error.

Figure 6:
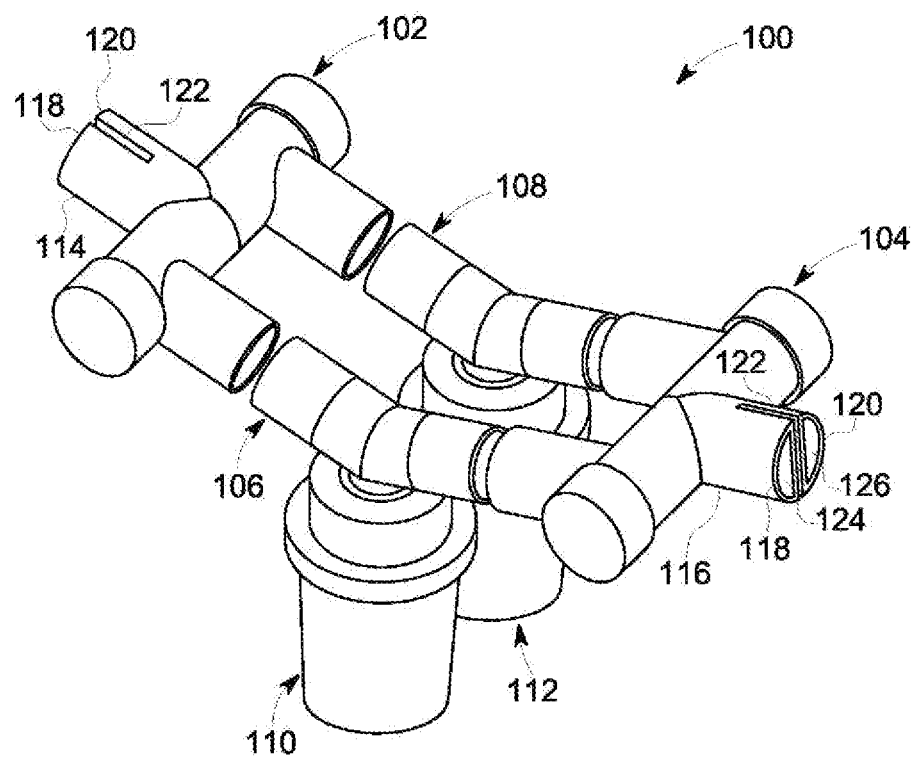
FIG. 6 is a perspective view of a fluid trap in accordance with an embodiment of the present invention.

Referring to FIG. 6, a dual-reservoir fluid trap 100 is shown in accordance with another embodiment. The fluid trap 100 comprises a first and second tube connector 102, 104, a first and second reservoir interface channel 106, 108, and a first and second reservoir 110, 112. The first and second tube connectors 102, 104 will hereinafter be described in accordance with the depicted embodiment as being adapted for insertion into separate dual lumen tubes, however alternate connections can be envisioned.

The tube connectors 102, 104 respectively comprise connector ends 114, 116. The connector ends 114, 116 each define a generally cylindrical exterior formed by two back-to-back, outward facing D-shaped portions 118, 120 with a gap 122 therebetween. The D-shaped portions 118, 120 are hollow and respectively define interior passages 124, 126. The interior passages 124, 126 are discrete in order to maintain separation between transferred gases. The interior passages 124, 126 are each in fluid communication with one of the reservoir interface channels 106, 108. Gravity directs fluid from the lumen 26, 28 through one of the interior passages 124, 126, through a respective interface channel 106, 108, and into a respective reservoir 110, 112.

Figure 7:
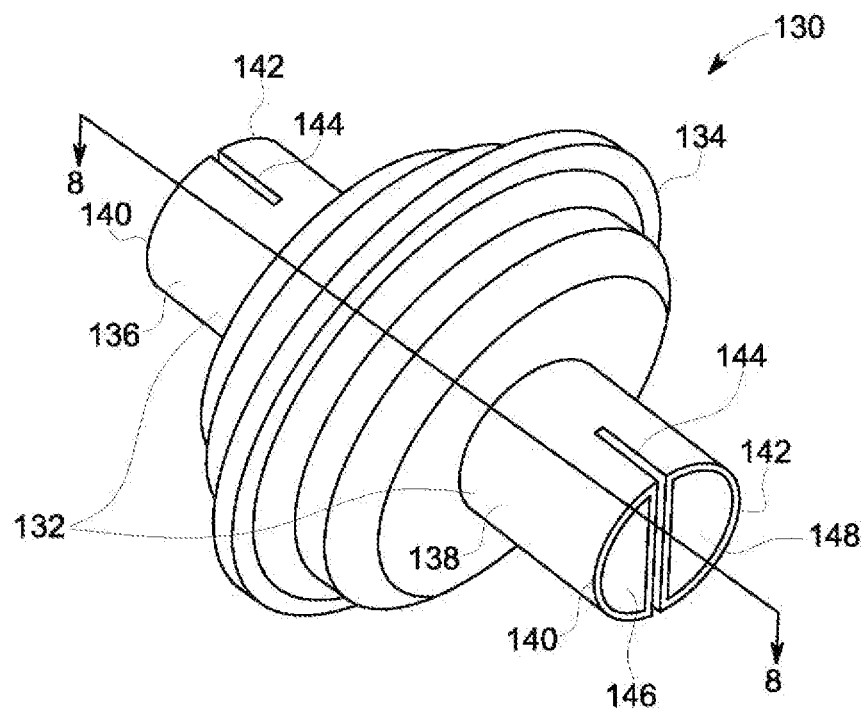
FIG. 7 is a perspective view of a fluid trap in accordance with an embodiment of the present invention.

Referring to FIG. 7, a dual-reservoir fluid trap 130 is shown in accordance with another embodiment. The fluid trap 130 comprises a tube connector 132, and a reservoir housing 134. The tube connector 132 comprises a first end 136 and a second end 138. The connector ends 136, 138 will hereinafter be described in accordance with the depicted embodiment as being adapted for insertion into separate dual lumen tubes, however alternate connections can be envisioned. The reservoir housing 134 may comprise a generally hollow cylindrical design.

The connector ends 136, 138 define a generally cylindrical exterior formed by two back-to-back, outward facing D-shaped portions 140, 142 with a gap 144 therebetween. The D-shaped portions 140, 142 are hollow and respectively define interior passages 146, 148. The interior passages 146, 148 are discrete in order to maintain separation between transferred gases.

Figure 8:
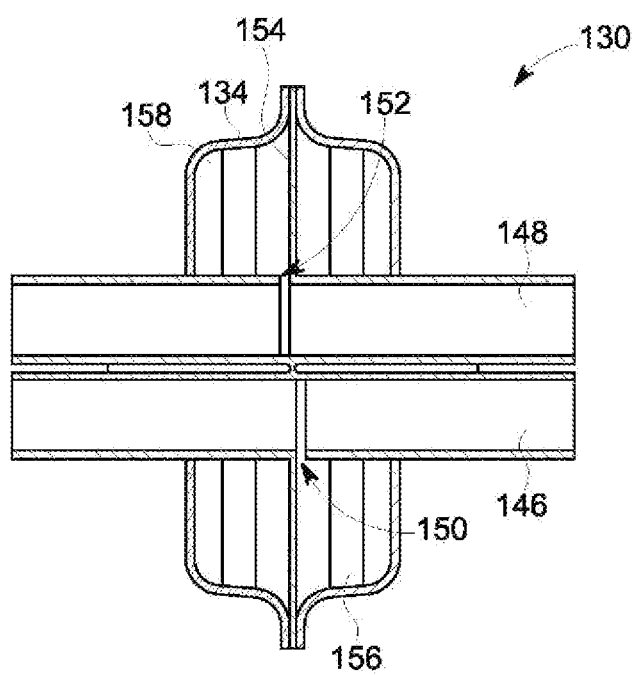
FIG. 8 is a cross-sectional view of the fluid trap in FIG. 7 in accordance with an embodiment.

Referring to FIG. 8, a sectional view of the fluid trap 130 through section 8-8 of FIG. 7 is shown in accordance with an embodiment. The interior passage 146 is in fluid communication with an aperture 150, and the interior passage 148 is in fluid communication with an aperture 152. The reservoir housing 134 comprises an interior partition 154 providing separate reservoirs 156 and 158. Aperture 150 is in fluid communication with reservoir 156, and aperture 152 is in fluid communication with reservoir 158. Gravity directs fluid from the lumen 26, 28, through one of the interior passages 146, 148, through a respective aperture 150, 152, and into a respective reservoir 156, 158.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A fluid trap, comprising:
   a reservoir housing defining a reservoir;
   a tube connector disposed through the reservoir housing, the tube connector comprising:
      a first connector end extending outward from a first side of the reservoir housing; a second connector end extending outward from a second side of the reservoir housing;
      an interior passageway in fluid communication with the first connector end and the second connector end;
      an aperture defined by the interior passageway, the aperture in fluid communication with the reservoir,
   wherein the reservoir housing and the tube connector are coaxial; and
   an interior partition dividing the reservoir into a first reservoir and a second reservoir.

2. The fluid trap of claim 1, wherein the tube connector comprises a first connector portion at each of the first and second connector ends, the first connector portion including the interior passageway.

3. The fluid trap of claim 2, wherein the first connector portion is adapted for insertion into a first lumen of a dual lumen tube such that the interior passageway is in fluid communication with the first lumen.

4. The fluid trap of claim 3, wherein the aperture is configured to direct fluid received from the first lumen via the interior passageway into to reservoir.

5. The fluid trap of claim 4, wherein the fluid is gravity fed from the first lumen to the reservoir.

6. The fluid trap of claim 1, wherein one of the first and second connector ends defines a cylindrical exterior.

7. The fluid trap of claim 1, wherein the first and second connector ends respectively extend orthogonally outward from the first and second sides of the reservoir housing, and wherein the first and second sides of the reservoir housing are parallel and opposite one another.

8. The fluid trap of claim 1, wherein the interior passageway comprises a first interior passageway defining a first aperture coupled to the first reservoir and a second interior passageway defining a second aperture coupled to the second reservoir.

9. The fluid trap of claim 8, wherein the first and second interior passageways have no fluid communication therebetween.

10. The fluid trap of claim 8, wherein each of the first and second interior passageways are in fluid communication with each of the first and second connector ends.

11. The fluid trap of claim 8, wherein the first and second interior passageways are separated from each other by a first gap defined between a first portion of the first and second interior passageways and a second gap defined between a second portion of the first and second interior passageways.

12. The fluid trap of claim 11, further comprising a wall coupled between the first and second interior passageways, the wall separating the first and second gaps.

13. The fluid trap of claim 8, wherein the first and second apertures are disposed adjacent the interior partition of the reservoir housing.

14. The fluid trap of claim 8, wherein the tube connector comprises a first connector portion and a second connector portion at each of the first and second connector ends, the first connector portion including the first interior passageway and adapted for insertion into a first lumen of a dual lumen tube such that the first interior passageway is in fluid communication with the first lumen, and the second connector portion including the second interior passageway and adapted for insertion into a second lumen of the dual lumen tube such that the second interior passageway is in fluid communication with the second lumen.

15. The fluid trap of claim 14, wherein the tube connector defines a gap between the first and second connector portions, the gap configured to accommodate a dual lumen tube partition.

16. The fluid trap of claim 15, wherein the first and second apertures are disposed adjacent the interior partition of the reservoir housing.

17. A fluid trap, comprising:
   a cylindrical reservoir housing defining a plurality of reservoirs fluidly separated by an interior partition; and
   a tube connector disposed coaxially through the reservoir housing, the tube connector comprising:
      a first connector end extending outward from a first side of the reservoir housing; a second connector end extending outward from a second side of the reservoir housing;
      a plurality of interior passageways in fluid communication with the first connector end and the second connector end, the plurality of interior passageways fluidly separated from one another; and
      a plurality of apertures, each aperture defined by one of the plurality of interior passageways and in fluid communication with one of the plurality of reservoirs.

18. The fluid trap of claim 17, wherein the tube connector comprises a plurality of connector portions at each of the first and second connector ends, each connector portion including one of the plurality of interior passageways and adapted for insertion into and in fluid communication with a separate lumen of a multiple lumen tube.

19. The fluid trap of claim 17, wherein each aperture is configured to direct gravity fed fluid received from its associated lumen via its associated interior passageway into to its associated reservoir.

\* \* \* \* \*